United States Patent [19]

Wittkampf et al.

[11] 4,373,531
[45] Feb. 15, 1983

[54] APPARATUS FOR PHYSIOLOGICAL STIMULATION AND DETECTION OF EVOKED RESPONSE

[75] Inventors: Frederik H. M. Wittkampf; Kornelis A. Mensink, both of Brummen; Hendrik L. Brouwer, Dieren, all of Netherlands

[73] Assignee: Vitafin N.V., Curacao, Netherlands Antilles

[21] Appl. No.: 231,882

[22] Filed: Feb. 5, 1981

Related U.S. Application Data

[63] Continuation-in-part of Ser. No. 30,457, Apr. 16, 1979, Pat. No. 4,305,396.

[51] Int. Cl.³ .............................................. A61N 1/36
[52] U.S. Cl. ....................... 128/419 PG; 128/419 PT
[58] Field of Search .................... 128/419 PG, 419 PT

[56] References Cited

U.S. PATENT DOCUMENTS

| | | | |
|---|---|---|---|
| 3,563,247 | 2/1971 | Bowers | 128/422 |
| 3,683,934 | 8/1972 | Bukowiecki et al. | 128/419 PG |
| 3,835,865 | 9/1974 | Bowers | 128/419 P |
| 3,845,773 | 11/1974 | Fontaine et al. | 128/419 PG |
| 3,881,493 | 6/1975 | Cannon | 128/419 PG |
| 3,924,641 | 12/1975 | Weiss | 128/419 PG |
| 4,055,189 | 10/1977 | Averbach et al. | 128/419 PG |
| 4,114,627 | 9/1978 | Lewyn et al. | 128/419 PT |
| 4,170,999 | 10/1979 | Allen et al. | 128/419 PG |

FOREIGN PATENT DOCUMENTS 2520730 11/1975 Fed. Rep. of Germany ...... 128/419 PG

*Primary Examiner*—William E. Kamm
*Attorney, Agent, or Firm*—Woodcock, Washburn, Kurtz, Mackiewicz & Norris

[57] ABSTRACT

A physiological stimulating system includes improved means for minimizing the polarization that results at the stimulus site, thereby enabling enhanced detection of evoked responses. In the pacemaker embodiment, the stimulus signal comprises positive recharge pulses immediately before and immediately after the negative stimulus signal, the recharge pulses being adapted in a time duration and amplitude such that the total current delivered to the stimulus site, (e.g., a patient's heart) by the stimulus signal is substantially zero.

17 Claims, 4 Drawing Figures

APPARATUS FOR PHYSIOLOGICAL STIMULATION AND DETECTION OF EVOKED RESPONSE

This application is a continuation-in-part of U.S. application Ser. No. 030,457, filed Apr. 16, 1979, issued Dec. 15, 1981 as U.S. Pat. No. 4,305,396, titled "Improved Rate Adaptive Pacemaker". All of the disclosure of that application is incorporated herein by reference.

BACKGROUND OF THE INVENTION

This invention lies in the field of physiological stimulus systems, e.g. pacemaker systems, and in particular implantable systems for physiological stimulation and detection of the response evoked by stimulation.

For the operation of conventional demand type pacemakers, it is necessary to sense the natural QRS signals which are developed in the ventricle, so as to cause resetting of the pacemaker oscillator. The state of the art permits reliable sensing of the natural QRS signal, as is seen from the widespread use of demand pacers. It is noted that, in demand pacer operation, the QRS signal occurs at least a full heartbeat period following the last stimulus pulse, if any, such that conditions in the vicinity of the electrode are relatively quiescent. By contrast, immediately after delivery of a negative going stimulus pulse, there is a large polarization signal present at the electrode, due to the condition of the adjacent heart tissue cells and the effective capacitance of the electrode itself. Since it takes some time for this polarization signal to dissipate it has the effect of masking signals which occur shortly thereafter, e.g., the evoked QRS or evoked T wave signals.

The area of threshold tracking pacemakers best illustrates the problem generated due to the polarization signal at the electrode following delivery of a stimulus pulse. A threshold tracking system is illustrated in U.S. Pat. No. 3,920,024, incorporated herein by reference. To date, there has been no significant commercial use of the implantable threshold tracking pacer, primarily due to the difficulty of detecting the resulting evoked signal in the midst of the polarization signal. Threshold tracking pacers are discussed at length in the literature, and there has been a limited use of external threshold tracking pacers, for various clinical applications. However, they have not achieved the prominence that was predicted some years back, due to the essentially unsolved problem of reliably and accurately picking the evoked QRS signal out of the overall signal which is present at the electrode shortly after delivery of the stimulus. It is clear that the inability to accurately and reliably sense the presence or absence of an evoked heartbeat is critical to the performance of a threshold tracking pacemaker.

The advantage of the threshold tracking pacemaker has been questioned recently, due to the greatly increased power capacity of the lithium battery as compared to prior mercury zinc batteries. The threshold tracking pacemaker would save a considerable amount of energy, and thereby extend pacer lifetime substantially, due to the fact that stimulus pulses would be delivered at or near threshold, instead of at a level which provided a safety factor of 2 or 3 times. Since present day lithium batteries extend the pacer lifetime to 12 to 15 years, this foreseen relative advantage of the threshold tracking pacemaker is greatly attenuated. However, other developments which are foreseeable continue to make it desirable to achieve a solution which would permit a reliable threshold tracking pacemaker. The ability to monitor threshold and to process information obtained from the evoked heartbeat may be quite useful in future pacemaker models, such as for providing a diagnostic aid in determining patient condition. As set forth in the referenced patent application, monitored patient threshold may be used to control the rate of delivery of stimulus signals. Also, changes in electrode construction and improvements in programmability are expected to enhance the value of threshold tracking and, more generally, the value of being able to continuously monitor both evoked and natural heartbeat signals.

While the utility of the subject invention is best described in the pacemaker, or pacing system embodiment, it is to be understood that the invention has utility in other systems for physiological stimulation. The invention may be practiced in any application where it is desired to quickly determine the physiological response to an applied stimulus by detection of the resulting evoked electrical characteristic at the location of applied stimulus.

SUMMARY OF THE INVENTION

It is an object of this invention to provide a pacing system for delivering stimulus signals to a patient's heart, wherein the sensed polarization immediately following delivery of a stimulus signal is minimized.

It is another object of this invention to provide a pacing system which enables quicker and more accurate sensing of an evoked response following delivery of a stimulus.

It is another object of this invention to provide an improved pacing system and method for threshold tracking.

It is another object of this invention to provide an improved pacemaker system for sensing heartbeat signals substantially immediately following delivery of stimulus signals, the system providing for delivery of recharge pulses of optimum level and timing so as to balance out the polarization effect of a delivered stimulus signal.

In accordance with the above, there is provided an improved system for delivery of physiological stimulus signals, such as a cardiac pacemaker, which system is characterized by having output means for providing a stimulus signal, each of said signals being constituted of a series of alternating polarity pulses of respective time durations and signal levels so as to minimize the resulting polarization at the point of delivery of such signals. In particular, the stimulus signal of this invention comprises a first recharge pulse of positive polarity, followed by a negative stimulus pulse and then a succeeding positive recharge pulse, the series of pulses having a time duration which is very small compared to the time period between delivered stimulus signals.

DESCRIPTION OF THE PREFERRED EMBODIMENT

Figure 1:
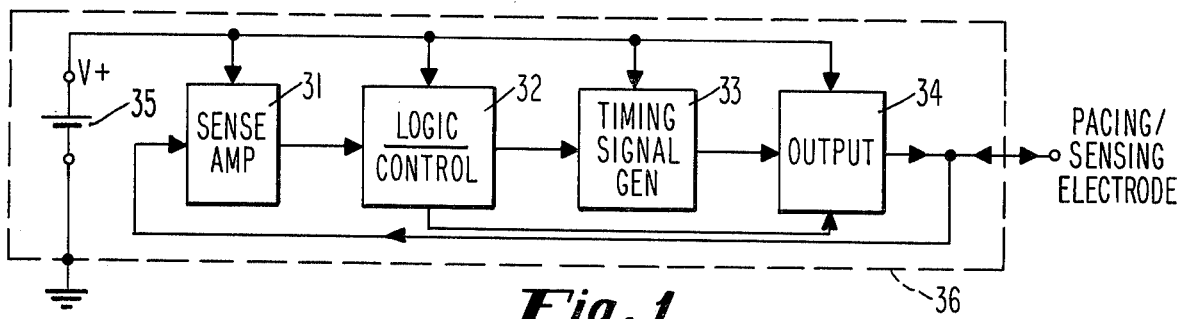
FIG. 1 is a block diagram showing the primary components of a pacing system utilizing this invention.

Referring now to FIG. 1, there is shown a block diagram illustrating the essential components of the pacing system utilizing this invention. The invention is illustrated in terms of a demand pacer, the features of which are well known in the art. A sense amplifier 31 detects the presence of a QRS signal, and connects a signal to a logic/control circuit 32 when a QRS has been sensed. In a threshold tracking embodiment, such as illustrated in U.S. Pat. No. 3,920,024, amplifier 31 must detect the evoked response which follows the stimulus in about 10 to 50 ms. The circuitry of block 32 performs the normal logic functions of a demand pacer such as distinguishing a sensed natural QRS signal, timing out a refractory interval, etc. For programmable pacemakers, stored information relative to pacing parameters and other program control features may be considered to be found in block 32. Also, block 32 suitably contains the desired circuitry for employing the evoked response information, e.g., tracking threshold. As illustrated, control signals may be transferred from block 32 to output 34, for controlling the output in accordance with programmed signals or for threshold tracking. Block 33 is the basic timing generator, which establishes the rate at which the pacer delivers stimulus pulses in the absence of natural patient pulses. As is known in the art, if the timing generator times out on its own, meaning that a stimulus is to be delivered, the timing signal is connected to an output circuit 34. If a signal comes from circuit 32 prior to time out in circuit 33, which signal indicates that a natural QRS has been detected, the timing generator 33 is reset without triggering an output. Output 34 represents circuitry which is utilized in generating a desired output signal, commonly referred to as an output pulse, of desired value in terms of pulse width, voltage or current. As shown further in FIG. 1, the output 34 is connected to a pacing/sensing electrode which is the end of a pacing lead (not shown), which lead provides the necessary electrical connection between the pacemaker and the patient's heart. An electrical path is illustrated between the output of circuit 34 and the input of sense amplifier 31. Further, power is provided, suitably by a lithium type battery or any other desired source, as illustrated at 35. For unipolar pacing systems, the terminal of source 35 shown as ground is generally connected to the case of the pacemaker, illustrated at 36.

Figure 2A:
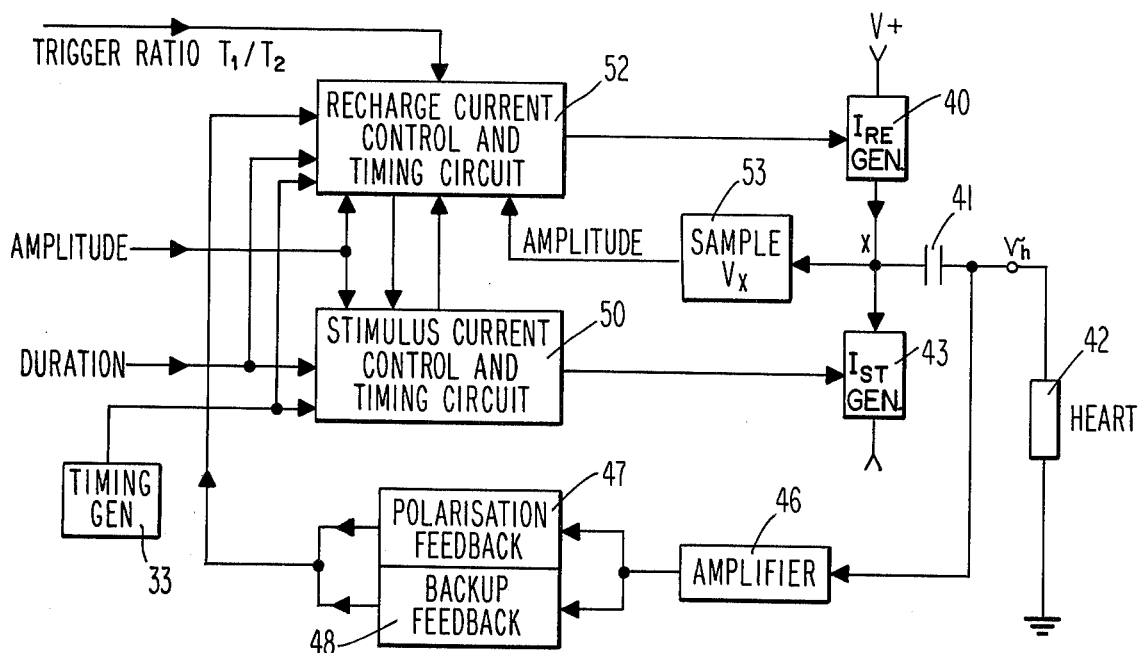
FIG. 2A is a block diagram showing a current control embodiment of the output stage of the system of this invention.

Referring now to FIG. 2A, there is shown a block diagram of an embodiment of output circuit 34 which is based upon current control of the component pulses of the delivered stimulus signal. As used in this application, the term "stimulus signal" shall refer to the group or series of pulses delivered, the negative going pulse of which is the component which actually provides the stimulus. Also, the term pulse is used in a general manner, it being understood that a pulse as actually generated and used within this invention is not confined to a sharp signal in the time domain, but may be a sloped, exponential or other form of nonlinear signal.

In FIG. 2A, the primary circuit components which generate the stimulus signal are the two current generators, namely the recharge current generator 40 and the stimulus generator 43. These two current generators are shown as ideal circuits and can be contructed in any conventional manner. They are suitably switchable on-off circuits, such that they can be turned on and off sharply, such as can be accomplished by putting a control voltage on the gate of a FET transistor or the like. When recharge current generator 40 is on; and stimulus current generator 43 is off, a current flows from V+ through the generator, through the capacitor 41 which charges up, and through the heart 42 to ground, thereby applying a positive polarity signal to the heart. When stimulus current generator 43 is on, and recharge generator 40 is off, current flows up through heart 42 as seen in the drawing, through capacitor 41 (thereby discharging it) and down through current generator 43, delivering a negative pulse to the heart. The size of the negative going pulse is designed, in accordance with well known principles, to evoke stimulation of the heart.

Figure 2B:
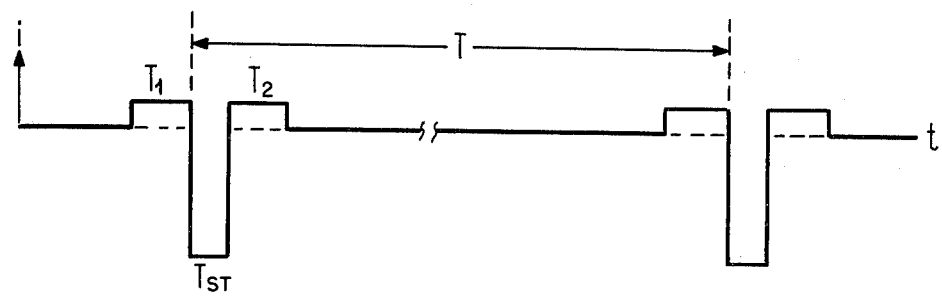
FIG. 2B is a curve depicting the timing of stimulus signals delivered by the system of this invention.
Figure 2C:
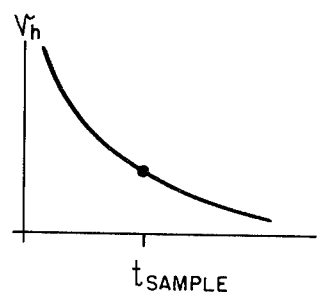
FIG. 2C is a curve illustrating the sampling of the polarization at the heart for use in the polarization feedback branch of the circuit of FIG. 2A.

As seen in FIG. 2B, recharge generator 40 is first triggered for a time $T_1$ to produce a first positive delivery of current to the heart, stimulus generator 43 is then turned on for a time $T_{st}$ to deliver the negative stimulating component, and then recharge generator 40 is turned on again for a time $T_2$ to deliver another recharge pulse. These three pulses, preferably time contiguous as shown, constitute the total stimulus signal which is delivered periodically by the pacemaker when no natural heart signal is detected.

In practice, the respective times $T_1$ and $T_2$ and the current levels of the recharge pulses are controlled by recharge current control and timing circuit 52. As shown, this circuit receives program information, suitably from block 32, for determining the ratio $T_1/T_2$, the amplitude of the recharge pulses, and the duration of each. In a similar manner, stimulus current control and timing circuit 50 controls the stimulus component delivered by current generator 43, and receives amplitude and duration program signals. Both circuits 52 and 50 receive basic timing signals from the timing generator 33, to determine when the series of pulses, or the overall stimulus signal is to be generated. As shown by the arrows between blocks 52 and 50, the timing signal may be connected from block 52 at the end of the first recharge pulse to trigger a stimulus pulse, and another timing signal may be connected from block 50 to 52 at the end of the stimulus pulse to trigger the second recharge signal. It is understood that timing circuitry is well known in the art, and the time durations $T_1$ and $T_2$ may be provided conveniently by one-shot or monostable multi-vibrators or their equivalent, or other digital timing mechanisms well known in the art.

The embodiment of FIG. 2A provides two or three feedback loops. Block 53 is shown connected to point X, between the two current generators, which block measures the voltage at such point X at a predetermined time between stimulus signals. By determining the variation, if any, of $V_X$, the circuit can measure whether the net charge delivered through capacitor 41 during the preceeding impulse group is zero. If, due to improper balancing between positive and negative output currents, or for any other reason of instability, $V_X$ has been changed, an amplitude feedback signal is applied to block 52 to change the value of the recharge current. As long as the total charge delivered by the two recharge pulses and the stimulus charge is substantially zero, the voltage at point X, as sampled between stimulus signals, will not vary significantly.

A second feedback branch is connected between the output at the heart and the recharge control circuit 52.

The heart voltage $V_h$ is sampled at a sample time shortly after termination of $T_2$, to determine the polarization level. The polarization level is compared to a reference at block 47, and an output signal connected to block 52 to change the ratio $T_1/T_2$ of the recharge pulses for succeeding stimuli. For further improvement the reference value can be related also to the stimulus duration ($T_{st}$) and/or amplitude. Changing the ratio of $T_1$ to $T_2$ changes the polarization decay characteristic, and by this means the residual polarization can be optimally reduced. A second branch 48 of this feedback loop samples $V_h$ following the delivery of a backup pulse for a threshold tracking system. It is to be understood that for a threshold tracking system where a series of backup pulses is delivered until response is evoked, $V_h$ may be monitored following each of such backup pulses.

For the circuit of FIG. 2A, the duration $T_1$ of the first recharge pulse is determined by the stimulus duration input, as well as the $T_1/T_2$ ratio information. The amplitude is determined by the program amplitude of the stimulus current, as well as the feedback through block 53. The stimulus pulse duration $T_{st}$ is determined by the stimulus duration information, while the stimulus amplitude is determined by the stimulus amplitude input. The second recharge pulse duration $T_2$ is determined by the $T_1/T_2$ ratio and by the stimulus duration input, while the amplitude is determined by the stimulus current input and by the feedback through block 53. It is important that the total charge of the two recharge pulses be substantially equal to the charge of the stimulus portion, such that the net charge delivered to the heart by the stimulus signal is substantially zero. It need not be precisely zero, since further recharge can be accomplished following recharge pulse $T_2$ and before the next stimulus signal. However, in order to minimize the polarization at the sensing electrode following the termination of the second recharge pulse, the net charge delivered by the three pulse components should be substantially zero. In practice, $T_1$ plus $T_2$ may be approximately 4 times $T_{st}$, although this ratio may go up to 10 or more. It is, however, important that the second recharge pulse not be too long, since the evoked response can hardly be sensed until the second recharge pulse is terminated. Conversely, there is a limit in the amplitude of the two recharge pulses, since it has been found that if these pulses are made too high in amplitude this causes some reduction in the stimulation efficiency.

The advantage of the circuit of FIG. 2A is that the polarization is compensated for very accurately. This is an active system which measures the polarization, and forces adjustments through the feedback loops so as to reduce the polarization to a minimum. The disadvantages are the use of two or more feedback systems, and the extra current consumption due to the complexity of the circuit.

Figure 3A:
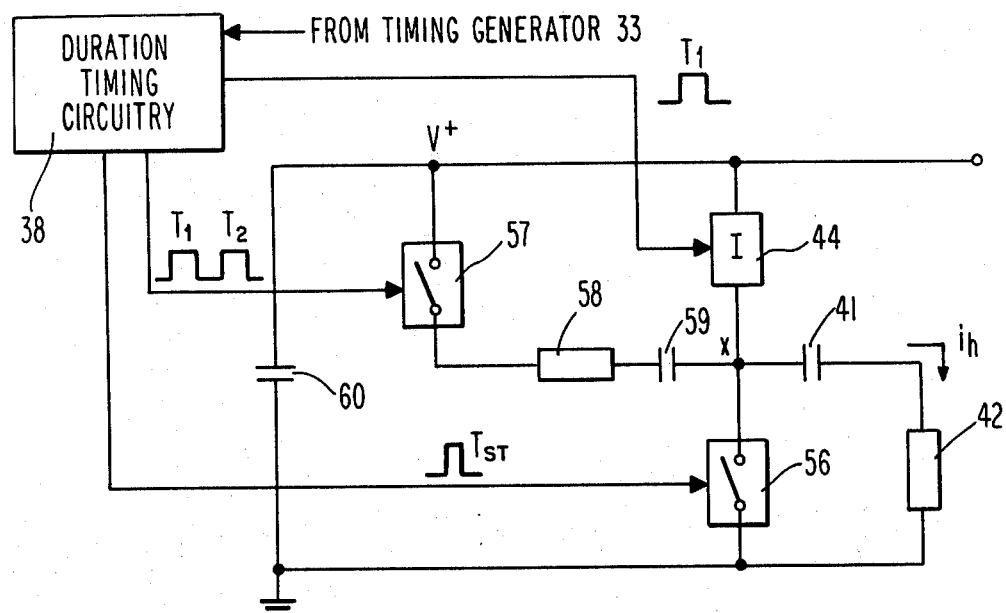
Figure 3B:
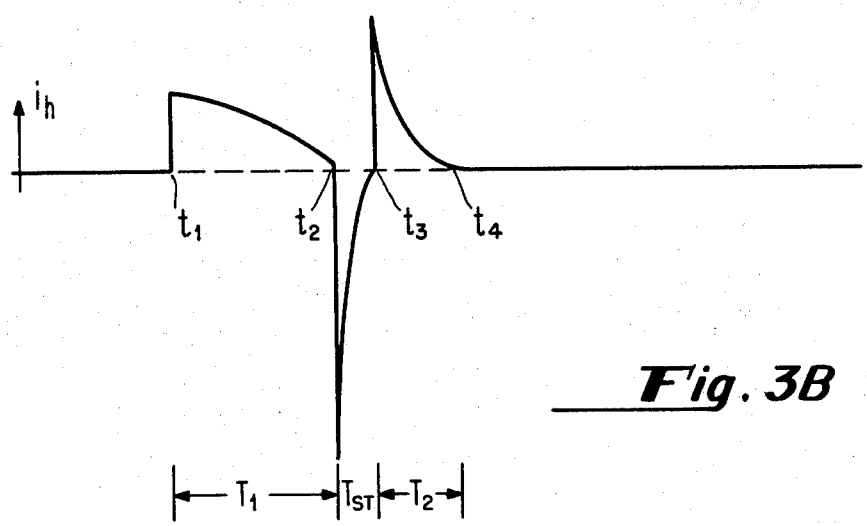
Figure 3C:
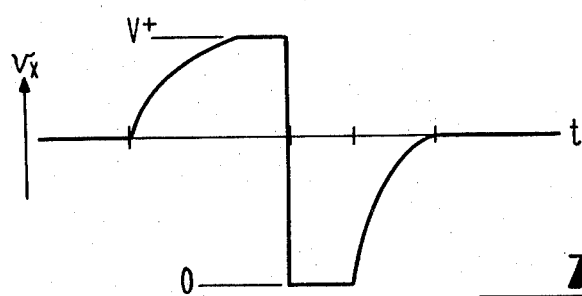

Reference is made to co-pending application Ser. No. 231,889, filed on the same date as this application, and issued Aug. 10, 1982 as U.S. Pat. No. 4,343,312, which shows a preferred embodiment of an output circuit of this invention in FIGS. 3A, 3B and 3C thereof.

While it has been determined that the 3 pulse arrangement provides excellent improvement in reducing the detected polarization following stimulus, improvement is accomplished by utilizing a positive recharge pulse prior to the negative stimulus pulse, even without a second recharge pulse. Such a recharge pulse is suitably no more than 10 ms, since a natural QRS can hardly be sensed during the recharge pulse. If a second recharge pulse is utilized, it is preferably of short time duration, so that the evoked response can be sensed as quickly as possible.

We claim:

1. A pacemaker of the type for delivering pacing stimulus signals to a patient, having an output to which generated stimulus signals are connected, a timing generator for timing the generation of pacing stimulus signals, output means for generating said pacing stimulus signals and delivering same to said output, sensing means for sensing heartbeat signals from said patient, and logic means connected to said sensing means and said timing generator for controlling generation of said pacing stimulus signals, wherein said output means is characterized by duration means for generating output signals having three separate durations, said output means having first means for generating a first recharge pulse of a positive polarity and a first duration, second means for generating a stimulus pulse of a negative polarity and a second duration following said first duration, and a third means for generating a second recharge pulse of a positive polarity and a third duration following said second duration, said three pulses together comprising one of said stimulus signals.

2. The pacemaker as described in claim 1, comprising timing means for controlling the time and sequence of the said three durations, said timing means controlling said three durations such that each successive duration is contiguous with the preceeding one.

3. The pacemaker as described in claim 1, wherein said output means comprises means to control the ratio of said third duration to said first duration.

4. The pacemaker as described in claim 1, wherein said output means comprises means to control the total charge of said first and third pulses to be substantially equal to that of said stimulus pulse.

5. A pacing system for delivering pacing signals to a patient's heart, comprising:
   a. lead means for delivering output signals to said heart and for sensing heart signals representative of said patient's heart activities;
   b. a pacemaker for generating pacing signals, having an output connected to said lead means for connecting said pacing signals thereto; and
   c. said pacemaker having output signal means for generating both positive and negative output pulses, said signal means including timing means for timing at least two of said positive pulses with one of said negative pulses in a given time relationship to form each of said pacing signals at said output, and signal initiation means for periodically initiating generation of said pacing signals.

6. The pacing system as described in claim 5, wherein said output signal means generates pacing signals comprising a first positive recharge pulse followed in time by a negative stimulus pulse and then a second positive recharge pulse.

7. The pacing system as described in claim 6, wherein said output signal means generates said pulses contiguous in time.

8. The pacing system as described in claim 6, wherein said output signal means comprises means for controlling the charge in said two positive pulses to be substantially equal to the charge in said negative pulse.

9. The pacing system as described in claim 5, comprising means to vary the relative time duration of said at least two positive signals.

10. The pacing system as described in claim 5, comprising means to vary the energy contained in each of said positive and one negative output pulses.

11. The pacing system as described in claim 5, said pacemaker having an input means for receiving sensed heart signals, said input means comprising a current amplifier.

12. A stimulating system for delivering stimulating signals to a selected organ of a patient, said system having generator means for generating stimulating signals and lead means for connecting said stimulating signals from said generator means to said organ, said generator means being characterized by having output signal means for generating a prior positive pulse, a following negative pulse and a following positive pulse in a predetermined time sequence for each of said stimulating signals.

13. The system as described in claim 12, wherein said prior positive pulse is less than about 10 ms.

14. The system as described in claim 11, comprising means for sensing the evoked response of said organ following connecting of each stimulating signal thereto.

15. In a pacing system for delivering pacing signals to a patient's heart and for sensing responses evoked by said pacing signals, the method characterized by;
 a. periodically generating pacing signals, said generating of each pacing signal comprising generating at least two separate positive pulses and a negative pulse;
 b. delivering said periodically generated pacing signals to said heart; and
 c. sensing evoked heartbeat responses following each said delivered signal.

16. The method as described in claim 15, comprising generating a first positive pulse of a duration limited to about 10 ms, said negative pulse immediately following said first positive pulse.

17. The method as described in claim 15, comprising controlling the charge delivered by each of said pulses so that the total net charge in each said pacing signal is substantially zero.

* * * * *